(12) United States Patent
Zhang et al.

(10) Patent No.: US 8,755,875 B2
(45) Date of Patent: Jun. 17, 2014

(54) SYSTEM FOR HEART PERFORMANCE CHARACTERIZATION AND ABNORMALITY DETECTION

(75) Inventors: Hongxuan Zhang, Schaumburg, IL (US); Detlef W. Koertge, Carpentersville, IL (US); Dennis Steibel, Jr., Lake Zurich, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1050 days.

(21) Appl. No.: 12/418,260

(22) Filed: Apr. 3, 2009

(65) Prior Publication Data

US 2009/0281441 A1 Nov. 12, 2009

Related U.S. Application Data

(60) Provisional application No. 61/051,777, filed on May 9, 2008.

(51) Int. Cl.
*A61B 5/0452* (2006.01)

(52) U.S. Cl.
USPC .......................................................... 600/516

(58) Field of Classification Search
CPC ............................. A61B 5/0468; A61B 5/0452
USPC ......................................................... 600/516
See application file for complete search history.

(56) References Cited

U.S. PATENT DOCUMENTS

| 4,378,022 | A | 3/1983 | Suobank et al. |
| 4,721,114 | A | 1/1988 | DuFault et al. |
| 4,909,259 | A | 3/1990 | Tehrani |
| 5,121,065 | A | 6/1992 | Wagner |
| 5,291,140 | A | 3/1994 | Wagner |
| 5,382,913 | A | 1/1995 | Carson et al. |
| 6,061,410 | A | 5/2000 | Linz |
| 6,161,037 | A | 12/2000 | Cohen |
| 6,459,934 | B1 | 10/2002 | Kadhiresan |
| 6,615,083 | B2 * | 9/2003 | Kupper ........................... 607/25 |
| 6,731,972 | B2 | 5/2004 | Meyer et al. |
| 6,931,273 | B2 | 8/2005 | Groenewegen et al. |

(Continued)

OTHER PUBLICATIONS

Lawrence D. Sherman, "The frequency ratio: An improved method to estimate ventricular fibrillation duration based on Fourier analysis of the waveform", Resuscitation, vol. 69, Issue 3, pp. 479-486, Jun. 2006.

(Continued)

*Primary Examiner* — Joseph Stoklosa
(74) *Attorney, Agent, or Firm* — Brennan K Bradley (57) ABSTRACT

A system for heart performance characterization and abnormality detection includes an acquisition device for acquiring an electrophysiological signal representing heart beat cycles of a patient heart. A detector detects one or more parameters of the electrophysiological signal of parameter type comprising at least one of, (a) amplitude, (b) time duration, (c) peak frequency and (d) frequency bandwidth, of multiple different portions of a single heart beat cycle of the heart beat cycles selected in response to first predetermined data. The multiple different portions of the single heart beat cycle being selected from, a P wave portion, a QRS complex portion, an ST segment portion and a T wave portion in response to second predetermined data. A signal analyzer calculates a ratio of detected parameters of a single parameter type of the multiple different portions of the single heart beat cycle. An output processor generates data representing an alert message in response to a calculated ratio exceeding a predetermined threshold.

24 Claims, 8 Drawing Sheets

(56) References Cited

U.S. PATENT DOCUMENTS

| | | | |
|---|---|---|---|
| 7,031,764 B2 | 4/2006 | Schwartz et al. | |
| 7,123,954 B2 | 10/2006 | Narayan et al. | |
| 7,269,454 B2 | 9/2007 | Sherman | |
| 7,291,111 B2 | 11/2007 | Shertukde et al. | |
| 7,330,750 B2 * | 2/2008 | Erkkilä et al. | 600/509 |
| 7,499,744 B2 * | 3/2009 | Carlson et al. | 600/519 |

OTHER PUBLICATIONS

Christopher J. O'Connor, MD, Hansen Mansy, PHD, Robert A. Balk, MD, Kenneth J. Tuman, MD, and Richard H. Sandler, MD, "Identification of Endotracheal Tube Malpositions Using Computerized Analysis of Breath Sounds via Electronic Stethoscopes", Anesth Analg, 2005; vol. 101, p. 735-739.

Yunfan Gong, and David J. Christini, "Functional reentrant waves propagate outwardly in cardiac tissue" Physics Letters A, vol. 331, Issues 3-4, Oct. 18, 2004, pp. 209-216.

Tsu-Juey Wu, MD; Shien-Fong Lin, PHD; James N. Weiss, MD; Chin-Tai Ting, MD, PHD; Peng-sheng Chen, MD, "Two Types of Ventricular Fibrillation in Isolated Rabbit Hearts—Importance of Excitability and Action Potential Duration Restitution" Circulation, 2002, vol. 106, p. 1859-1866.

Abboud S, Zlochiver S., "High-frequency QRS electrocardiogram for diagnosing and monitoring Ischemic heart disease", J Electrocardiol, Jan. 2000, vol. 39, No. 1, p. 82-86.

* cited by examiner

| SIGNAL | P WAVE PORTION | QRS COMPLEX PORTION | ST SEGMENT PORTION | T WAVE PORTION | U WAVE PORTION |
|---|---|---|---|---|---|
| P WAVE PORTION | --- | P vs. QRS | P vs.ST | P vs. T | P vs. U |
| QRS COMPLEX PORTION | QRS vs. P | --- | QRS vs.ST | QRS vs. T | QRS vs. U |
| ST SEGMENT PORTION | ST vs. P | ST vs. QRS | --- | ST vs. T | ST vs. U |
| T WAVE PORTION | T vs. P | T vs. QRS | T vs.ST | --- | T vs. U |
| U WAVE PORTION | U vs. P | U vs. QRS | U vs.ST | U vs. T | --- |

SYSTEM FOR HEART PERFORMANCE CHARACTERIZATION AND ABNORMALITY DETECTION

This is a non-provisional application of provisional application Ser. No. 61/051,777 filed May 9, 2008, by H. Zhang et al.

FIELD OF THE INVENTION

This invention concerns a system for heart performance characterization and abnormality detection by calculating ratios of detected parameters of multiple portions of a single heart beat cycle of an electrophysiological signal.

BACKGROUND OF THE INVENTION

Different portions of cardiac electrophysiological signals represent activities and functions of different cardiac tissue and circulation systems. Usually, surface ECG signal analyses based on electrophysiological activity (such as ECG signals and intra-cardiac electrograms) and time domain parameters of waveforms are utilized for cardiac arrhythmia detection and diagnosis, such as P wave distortion for detection of atrial fibrillation (AF) and ST segment changes for myocardial ischemia and infarction. However, known systems for cardiac arrhythmia identification and analysis based on ECG signals are subjective and need extensive expertise and clinical experience for accurate interpretation and appropriate cardiac rhythm management. Early arrhythmia recognition and characterization of myocardial ischemia and infarction, for example, is desirable for rhythm management of cardiac disorders and irregularities. Known systems analyze waveform morphologies and time domain parameters associated with cardiac depolarization and repolarization, such as P wave, QRS complex, ST segment, T wave, for cardiac arrhythmia monitoring and identification. Some known systems apply sophisticated mathematical theories to biomedical signal interpretation, such as for frequency analysis, symbolic complexity analysis and nonlinear entropy evaluation, and generate a pathology index for qualitative cardiac arrhythmia characterization. The known systems fail to provide adequate information on tissue mapping and arrhythmia localization and are subjective and burdensome to use for clinical data interpretation and proper cardiac rhythm management.

Known systems typically analyze time characteristics (amplitude, latency) or frequency domain (power, spectrum) changes but these often fail to accurately capture and characterize small signal changes in a portion (P wave, QRS complex, ST segment) of a heart beat cycle. Consequently, known systems may fail to detect arrhythmia or initiate a false alarm (for example, or indicate a FN (false negative)). A percentage of false negative results represents patients who do have disease X, but for whom a screening test wrongly indicates they do not have disease X. Also known systems relying on amplitude (voltage) change detection may be inaccurate for cardiac function evaluation and pathology diagnosis. Time domain and frequency domain parameter based analysis fails to provide comprehensive detailed indication of severity of pathology, location of abnormal tissue (such as muscle, chamber) and fail to associate signal frequency variation with cardiac pathological functional changes and may not adequately capture a signal portion (such as a region of interest (ROI) in cardiac electrophysiological signals). Known systems are typically unable to quantitatively capture and characterize changes, and predict a pathological trend such as a pathology trend from low risk to medium, and then to high risk (severe and fatal) rhythm (especially a VT growing arrhythmia). Further, noise and artifact sensitivity and stability impairs arrhythmia detection of known cardiac function monitoring systems. A system according to invention principles addresses these deficiencies and related problems.

SUMMARY OF THE INVENTION

A system improves precision and reliability of analysis and diagnosis of cardiac electrophysiological activities by calculating ratios of different portions of a cardiac signal to determine an accurate time, location and severity of cardiac pathology and events. A system for heart performance characterization and abnormality detection includes an acquisition device for acquiring an electrophysiological signal representing heart beat cycles of a patient heart. A detector detects one or more parameters of the electrophysiological signal of parameter type comprising at least one of, (a) amplitude, (b) time duration, (c) peak frequency and (d) frequency bandwidth, of multiple different portions of a single heart beat cycle of the heart beat cycles selected in response to first predetermined data. The multiple different portions of the single heart beat cycle being selected from, a P wave portion, a QRS complex portion, an ST segment portion and a T wave portion in response to second predetermined data. A signal analyzer calculates a ratio of detected parameters of a single parameter type of the multiple different portions of the single heart beat cycle. An output processor generates data representing an alert message in response to a calculated ratio exceeding a predetermined threshold.

DETAILED DESCRIPTION OF THE INVENTION

A system employs cardiac signal portion ratio analysis of cardiac electrophysiological signals (including surface ECG signals and intra-cardiac electrograms) to improve characterization and diagnosis of cardiac electrophysiological activities. The system calculates ratios of different portions of cardiac signals and uses predetermined mapping information to associate particular ratio values to a corresponding particular medical condition and determine an accurate time, location and severity of cardiac pathology and events. The system is used to accurately and reliably identify cardiac disorders, differentiate between cardiac arrhythmias, characterize pathological severity, predict life-threatening events, and evaluate drug delivery and treatment effects. The system extracts and characterizes arrhythmia pathology information in cardiac signals and compares and diagnoses a portion of cardiac signals indicating activities of heart tissue in a region of interest (ROI) using a ratio between P wave to QRS complex and ST segment to P wave, for example. The ratio values enable clinical cardiac status evaluation of a patient.

The system performs a signal portion multi-ratio based calculation and analysis to capture and characterize cardiac function related information and in one embodiment employs an artificial neural network (ANN). A signal portion ratio determination includes time domain signal portion ratio calculation (such as P wave vs. QRS complex, QRS complex vs. ST segment, for example) and frequency domain signal portion analysis (dominant frequency ratio, principal frequency peak ratio). The time domain analysis captures and characterizes signal distortion and cardiac functional abnormality in a signal pathway. Frequency portion ratio analysis is used to diagnose and characterize energy and excitation conduction and variation in cardiac chambers, tissue and circulation pathways. An ANN system is used for multi-parameter analysis and calculation and provides improved sensitivity and diagnosis stability for cardiac status monitoring and evaluation. The system signal portion ratio calculation and analysis advantageously employs relatively limited computation and power resources and may be implemented in a wide variety of patient monitors and implantable cardiac devices.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

Figure 1:
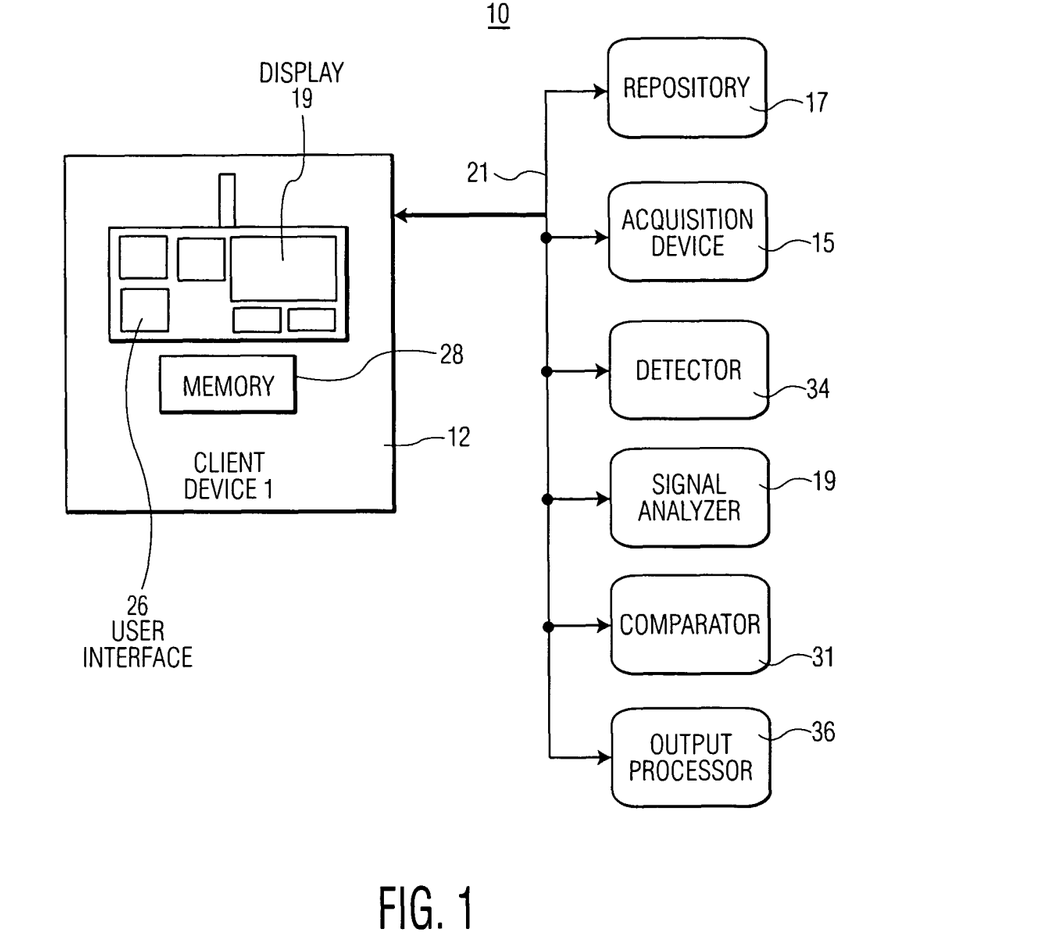
FIG. 1 shows a system for heart performance characterization and abnormality detection, according to invention principles.

FIG. 1 shows system 10 for heart performance characterization and abnormality detection. System 10 uses different portions of a cardiac signal to diagnose electrophysiological activities of the heart tissue and pathways. System 10 includes one or more processing devices (e.g., workstations, computers or portable devices such as notebooks, Personal Digital Assistants, phones) 12 that individually include memory 28, user interface 26 enabling user interaction with a Graphical User Interface (GUI) and display 19 supporting GUI and image presentation in response to predetermined user (e.g., physician) specific preferences. As well as device 12, system 10 also includes at least one repository 17, and electrophysiological signal acquisition device 15, signal analyzer 19, detector 34, comparator 31 and output processor 36 intercommunicating via network 21. In another embodiment these units may be embodied in one or more processing devices. Display 19 of processing device 12 presents display images comprising a GUI. At least one repository 17 stores electrophysiological data, patient parameters, derived parameters and calculated ratios. Repository 17 further includes mapping information associating particular ratio values with a corresponding particular medical condition and usable to determine an accurate time, location and severity of cardiac pathology and events. Repository 17 also includes medical image studies for patients in DICOM compatible (or other) data format. A medical image study individually includes multiple image series of a patient anatomical portion which in turn individually include multiple images.

Acquisition device 15 acquires an electrophysiological signal representing heart beat cycles of a patient heart. Detector 34 detects one or more parameters of the electrophysiological signal of parameter type comprising at least one of, (a) amplitude, (b) time duration, (c) peak frequency and (d) frequency bandwidth, of multiple different portions of a single heart beat cycle of the heart beat cycles selected in response to first predetermined data. The multiple different portions of the single heart beat cycle are selected from, a P wave portion, a QRS complex portion, an ST segment portion, a T wave portion and a U wave portion in response to second predetermined data, for example. Signal analyzer 19 calculates a ratio of detected parameters of a single parameter type of the multiple different portions of the single heart beat cycle. Output processor 36 generates data representing an alert message in response to a calculated ratio exceeding a predetermined threshold.

Figure 2:
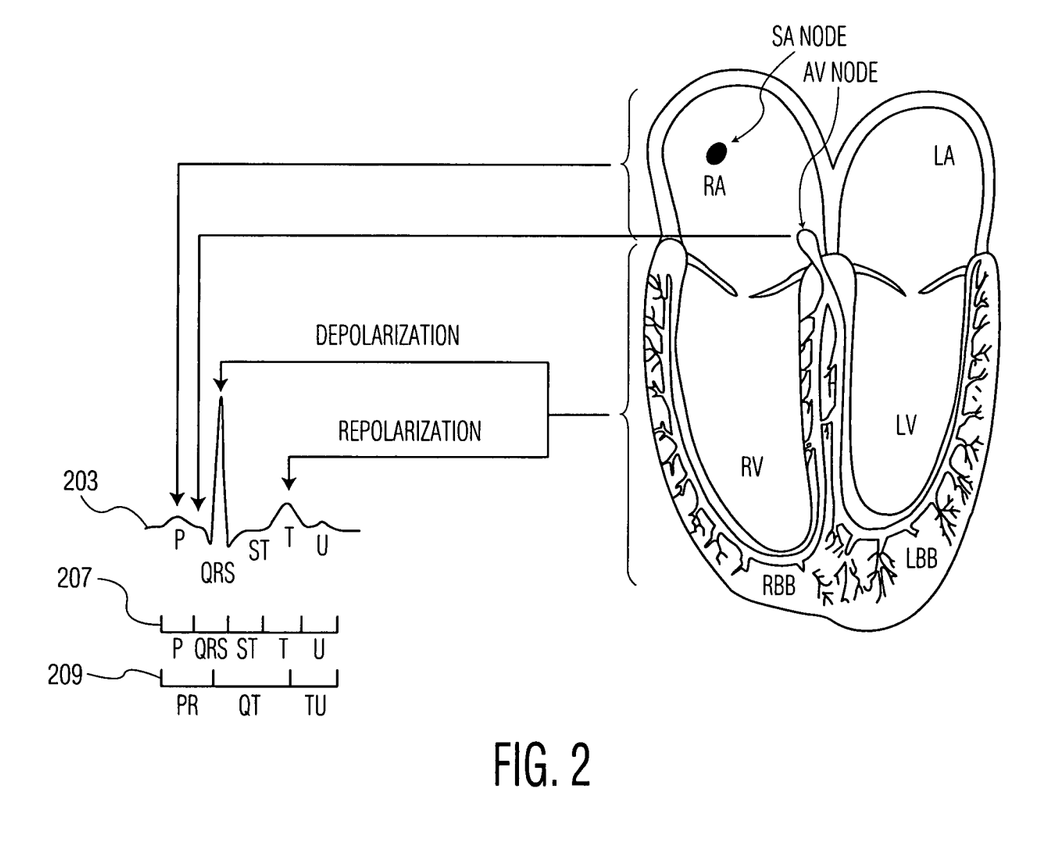
FIG. 2 illustrates cardiac conduction voltage potentials and corresponding regions responsible for the signals.

FIG. 2 illustrates cardiac conduction voltage potentials and corresponding regions responsible for the signals. Significant action related voltage potentials within a heart occur in two procedures, depolarization and repolarization, within the four heart chambers. The action voltage potentials accumulate and determine a heart electrogram 203, known as an ECG (from a body surface) or intra-cardiac electrograms. Hence different portions of electrograms represent cardiac activities of a corresponding heart area and tissue. For example, a P wave represents voltage potential and activities of atrial tissue and muscles while a QRS complex represents transition of cardiac excitation from atrium to ventricle. A single heart beat signal is segmented into different parts 207 including, P wave, QRS complex, ST segment, T wave, and U wave portions. In system 10 (FIG. 1) ratio calculation and computation is advantageously also performed on combinations of segments 209, including, PR segments, QT segments, TU segments and RT segments, for example. The calculated ratios indicate a comparison of different action (and voltage) potential regions and are advantageously used to identify a location of abnormality and arrhythmia.

Figure 3:
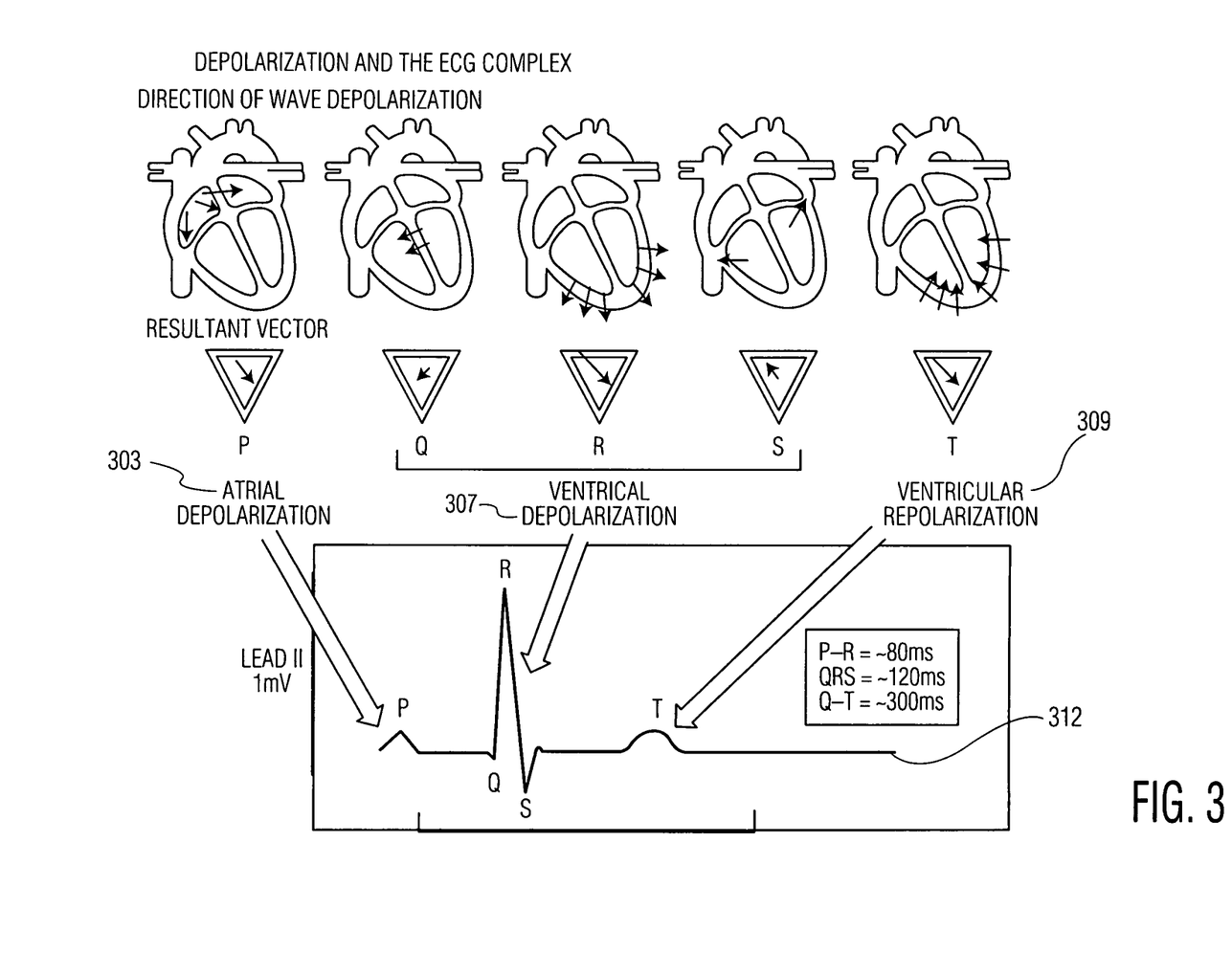
FIG. 3 illustrates a relationship between heart chamber, circulation and a cardiac electrogram signal.

FIG. 3 illustrates a relationship between heart chamber, circulation and a cardiac electrogram signal. Electrogram signal 312 is segmented in response to cardiac procedure type, specifically depolarization or repolarization types. A P-wave segment corresponds to atrial depolarization cardiac procedure 303, a QRS segment corresponds to ventricular depolarization cardiac procedure 307 and a T-wave segment corresponds to ventricular cardiac procedure 309. System 10 (FIG. 1) compares cardiac procedures and associated signal voltage ratios to determine time of occurrence within a heart cycle and cause of medical conditions.

Figure 4:
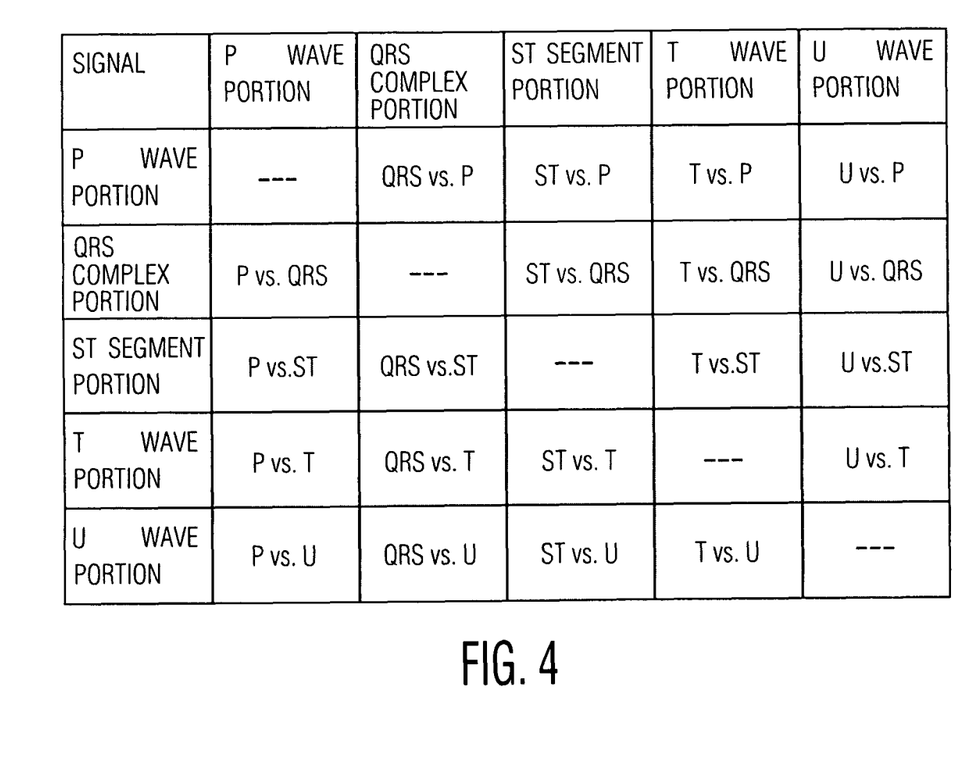
FIG. 4 shows a table indicating signal portion ratios used for heart performance characterization and abnormality detection, according to invention principles.

FIG. 4 shows a table indicating advantageous signal portion ratios calculated by signal analyzer 19 (FIG. 1) used for heart performance characterization and abnormality detection as well as cardiac function monitoring and analysis. System 10 detects and characterizes a cardiac malfunction by performing signal portion comparison using calculated ratios and by using mapping information associating particular ratio value ranges, cardiac location and demographic data (including age, weight, height, gender and pregnancy status) with cardiac malfunction and malfunction location in cardiac tissue. The mapping information further identifies a time of occurrence of a malfunction within a heart cycle, as well sequence and severity of the malfunction (e.g. an arrhythmia). System 10 continuously monitors signal portion ratio changes using different kinds of signal ratios for signal segment analysis and diagnosis to detect change in heart activity and functions (especially malfunction and arrhythmias, such as delayed conduction). System 10 compares parameters of a P wave and QRS wave (such as time interval, frequency, amplitude magnitude), for example, to provide a physician analytical information concerning a ratio between atrium and ventricle, facilitating medical condition detection and prediction.

Different cardiac signal portions represent electrophysiological activities occurring in different portions of a heart, such as P wave is associated with atrium activity. Signal analyzer 19 performs different kinds of analysis and indexing including determining, signal portion maximum amplitude in the time domain, signal portion time duration, signal portion spectrum, signal portion maximum amplitude in the frequency domain, bandwidth of a signal portion (e.g., 20-30 Hz) and signal portion energy. Signal analyzer 19 adaptively hierarchically prioritizes or weights signal analysis results and indexes for use in identifying particular medical conditions. Signal analyzer 19 adaptively selects one or more signal portion ratios to calculate, from the ratios of FIG. 4, such as P vs. QRS or QRS vs. P. Signal analyzer 19 automatically selects one or more ratios to calculate in response to data indicating a clinical application, procedure or medical condition being investigated and/or in response to user data entry. For example, for an Atrial Fibrillation (AF) condition, signal analyzer 19 selects P vs. QRS ratio since the QRS signal portion is stable. While for a ventricle Tachycardia condition, QRS vs. P may provide a better and more linear analysis. A ratio P wave vs. ST segment is usually utilized to detect and characterize myocardial ischemia and infarction, for example.

Signal analyzer 19 may also perform signal portion analysis using combined signal portions, such as a signal portion from P wave to R wave (PR portion) and a PT combined portion and a QU combined portion and other combined portions and ratios as indicated in Table I. The combined signal portions also comprise combinations of different signal portions determined by a user or automatically by signal analyzer 19 in response to data indicating a clinical application, procedure or medical condition being investigated and/ or in response to user data entry.

TABLE I

| Combined signal | PR Segment | QT Segment | TU Segment |
| --- | --- | --- | --- |
| PR Segment | — | QT vs. PR | TU vs. PR |
| QT Segment | PR vs. QT | — | TU vs. QT |
| TU Segment | PR vs. TU | QT vs. TU | — |

Signal analyzer 19 adaptively selects signal portions to use in ratio computation that are sensitive to arrhythmia or cardiac malfunction, for example, in response to data identifying a medical condition (such as a patient disease history in a medical record). Signal analyzer 19 uses both time domain and frequency domain based signal ratio calculation and analysis and calculates a time duration ratio of signal portions as a first index for use in analysis and quantification of cardiac status. Signal analyzer 19 also calculates other parameter ratios as indexes for arrhythmia localization and severity characterization, such as a spectrum ratio, dominant frequency ratio, peak amplitude or frequency value ratio and amplitude and frequency range ratios. The different kinds of signal portion ratio indexes and calculations are weighted and prioritized in one embodiment. An ANN based cardiac condition identification and decision system employs a combination of multi-index and ratio analysis. The tables of FIG. 4 and Table I show different kinds of combination of signal portions and corresponding ratios enabling signal analyzer 19 to track small changes in electrophysiological activities within cardiac tissue.

Figure 5:
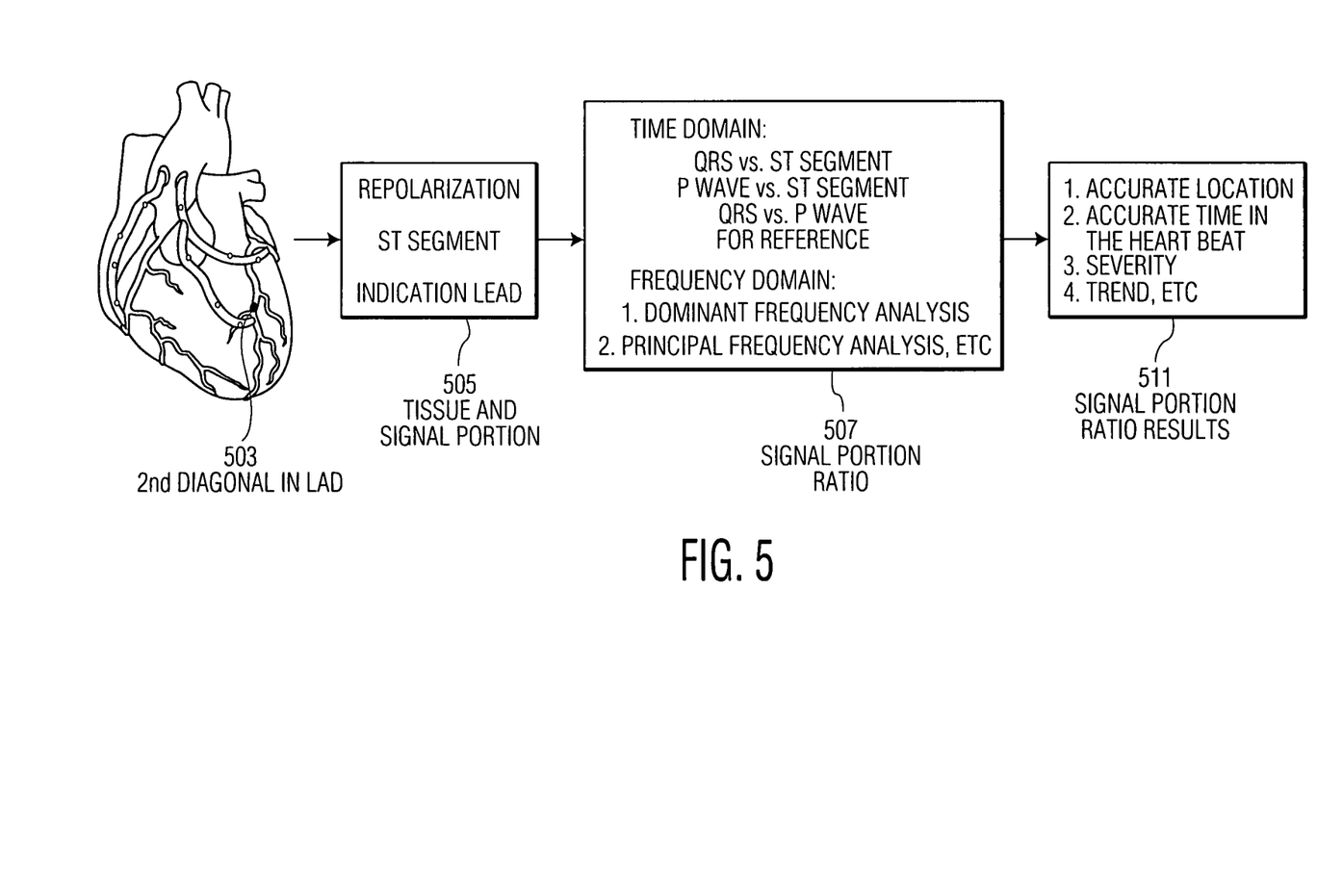
FIG. 5 illustrates signal portion ratio based analysis for a myocardial ischemia case which is at the second diagonal of LAD (left anterior descending) region, according to invention principles.

FIG. 5 illustrates signal portion ratio based analysis for a myocardial ischemia case which is in the second diagonal of LAD (left anterior descending) region circulation tissue 503. The example shows monitoring and detection in step 505 of a known cardiac arrhythmia and pathology during repolarization, for example, based on a corresponding ratio (such as ST segment vs. P wave). Signal analyzer 19 (FIG. 1) in step 507 calculates, in the time domain and frequency domain, an ST segment vs. QRS wave ratio of detected parameters of a single parameter type of different portions of a single heart beat cycle. In the time domain, the single parameter type comprises an amplitude or time duration and in the frequency domain comprises a dominant frequency or a principal frequency (as described later), for example. In step 511 signal analyzer 19 automatically identifies a particular medical condition indicated by calculated ratios using mapping information associating particular ratio value ranges, cardiac location and demographic data (including age, weight, height, gender and pregnancy status) with cardiac malfunction and malfunction location and severity in cardiac tissue. Thereby signal analyzer 19 detects and localizes an unknown cardiac disease within the cardiac tissue and detects a malfunction time of occurrence within a heart cycle and trend of the malfunction. The signal portion ratio analysis is applied to a single lead ECG signal (such as Lead I/II/III) as well as to multi-lead ECG and EP signals. Signal analyzer 19 uses multi-channel signal portion ratios and the mapping information associating ratios with cardiac locations to derive more detailed information and status of the cardiac tissue and function.

Figure 6:
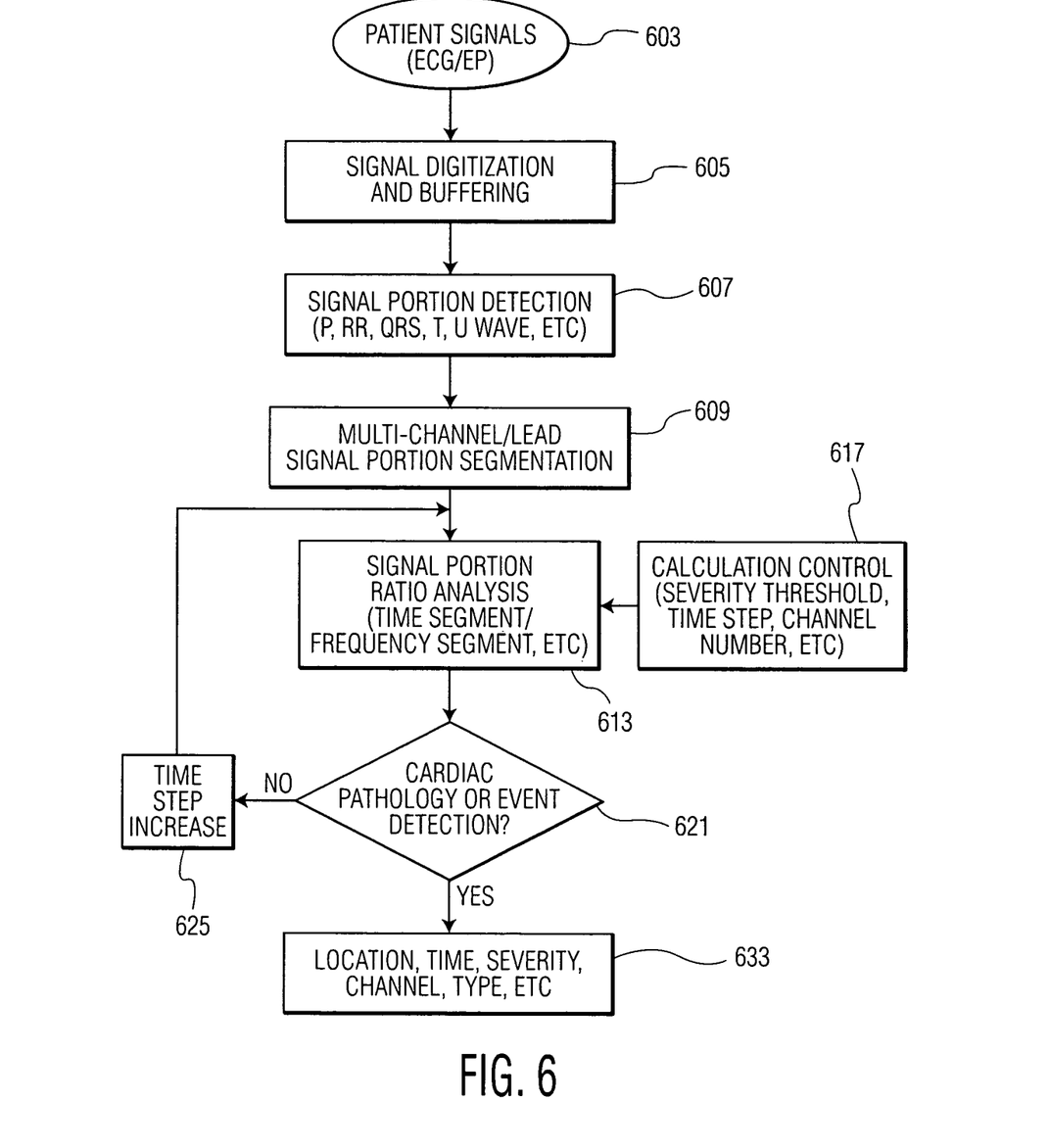
FIG. 6 shows a flowchart of process employing cardiac signal portion ratio analysis used by a system for heart performance characterization, according to invention principles.

FIG. 6 shows a flowchart of process employing cardiac signal portion ratio analysis used by system 10 (FIG. 1) for heart performance characterization. System 10 in step 603 acquires cardiac electrophysiological signals (including surface ECG signals or intra-cardiac electrograms). Cardiac signals, e.g., intra-cardiac electrograms are acquired from a multi-channel intra-cardiac catheter and digitized by a patient monitoring system and sent to system 10 in step 605. In step 607 detector 34 detects selected multiple different portions of a single heart beat cycle and in step 609, detector 34 detects one or more parameters of the digitized and buffered intra-cardiac electrograms of multiple different portions of a single heart beat cycle. Parameter types include, amplitude, time duration, peak frequency and frequency bandwidth, for example and the multiple different portions of the single heart beat cycle include, a P wave portion, a QRS complex portion, an ST segment portion, a T wave and a U wave portion.

In step 613, signal analyzer 19 calculates a ratio (selected from the ratios of FIG. 4 or Table I) of detected parameters of a single parameter type of the multiple different portions of the single heart beat cycle in response to predetermined settings provided in step 617. The predetermined settings include, a severity threshold, a calculation time step (time interval between ratio calculations of an intra-cardiac electrogram) and a channel number of the electrogram signal of a multi-channel (corresponding to multi-electrogram signal) intra-cardiac catheter. Signal analyzer 19 performs different kinds of signal portion ratio analysis in both the time domain (such as of P wave and the R wave) and frequency domain. In the frequency domain, signal analyzer 19 uses different methods of signal portion ratio calculation and computation. Signal analyzer 19 tracks a frequency ratio of different portions of a single heart beat cycle for ventricular tachycardia and fibrillation analysis and discrimination, for example. The ratio of first frequency peak (dominant frequency, 8-12 Hz) and second frequency peak (16-24 Hz) is used to capture atrial fibrillation events. The signal portion analysis and ratio calculation is not limited and encompasses different ratio ranges and is automatically adaptively varied in response to clinical application and characteristics of a cardiac disease.

Signal analyzer 19 calculates a dominant frequency ratio as follows.

$$Ratio_{Dominant\_frequency} = \frac{\int_\phi \text{dominant\_frequency}}{\int_\phi \text{signal\_frequency}}$$

Where, $\phi$ is frequency bandwidth of the dominant frequency, e.g. 20-45 Hz; $\varphi$ is a valid signal frequency range, e.g. 1-200 Hz. Signal analyzer 19 calculates a principal frequency ratio as follows.

$$Ratio_{Principal\_frequency} = \frac{\text{Frequency\_value}_{first\_peak}}{\text{Frequency\_value}_{second\_peak}}$$

Where, the ratio of the first and second frequency peaks correspond to two significant portions of cardiac signals. Further, variation in principal frequency ratio may indicate the occurrence of cardiac events.

In step 621, signal analyzer 19 identifies a particular medical condition by mapping determined calculated ratios to corresponding ratio value ranges associated with medical conditions using mapping information in repository 17. Signal analyzer 19 automatically identifies a particular medical condition indicated by calculated ratios of electrograms of individual signals of a multi-signal channel intra-cardiac catheter using mapping information associating particular ratio value ranges, cardiac location and demographic data (including age, weight, height, gender and pregnancy status) with cardiac malfunction and malfunction location and severity in cardiac tissue. In step 625, analyzer 19 changes calculation time step and steps 613, 621 and 625 are automatically iteratively repeated to identify a medical condition and associated characteristics for a predetermined limit number of iterations. Thereby in step 633 signal analyzer 19 detects and localizes an unknown cardiac disease within the cardiac tissue and detects a malfunction and trend of the malfunction for each electrogram of the multi-signal channel intra-cardiac catheter. Analyzer 19 determines location, severity and type of medical condition as well as time of occurrence within a heart cycle. Output processor 36 initiates generation of an alert message for communication in response to a calculated ratio exceeding a predetermined threshold.

Figure 7:
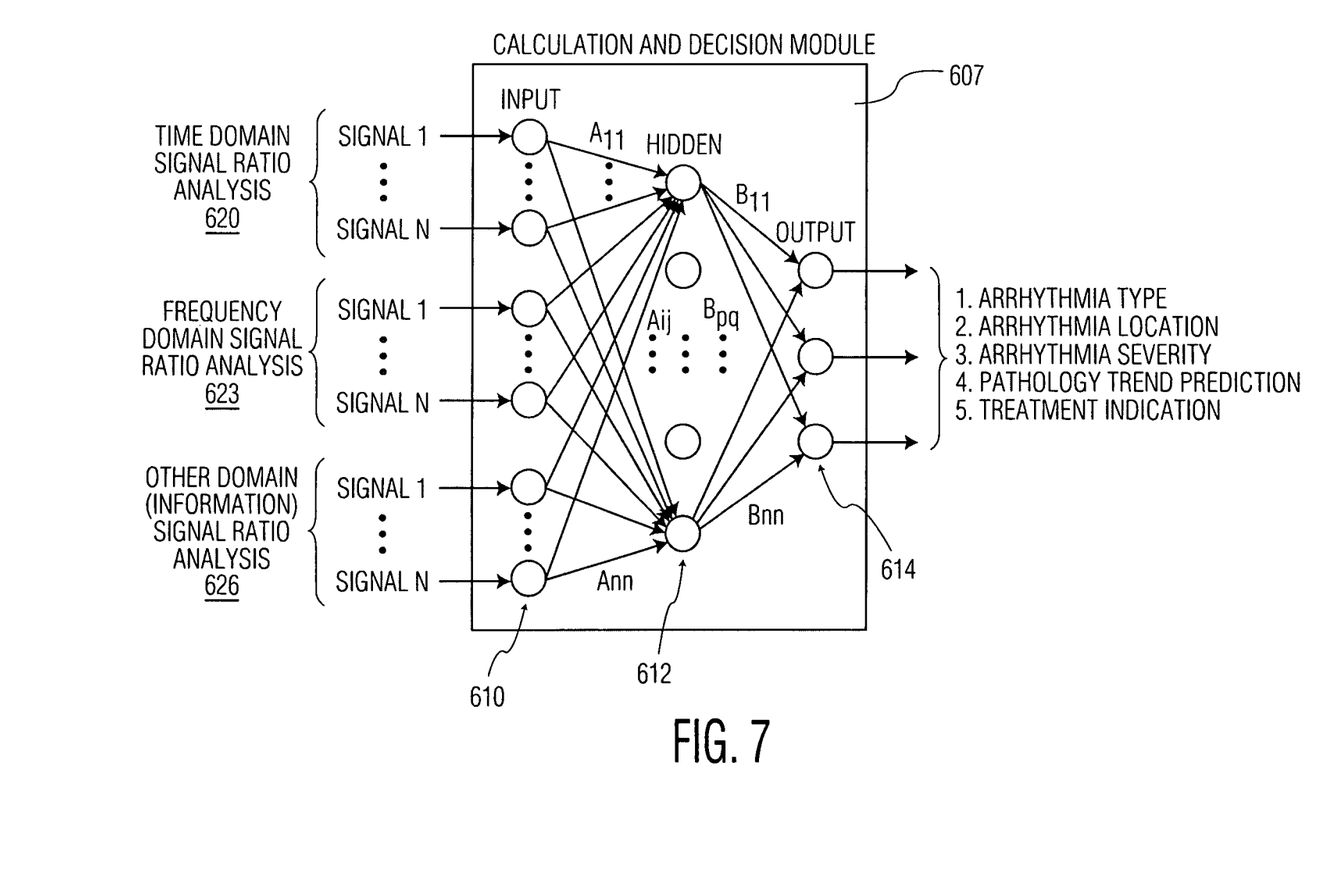
FIG. 7 shows an artificial neural network (ANN) employed in a system for heart performance characterization using cardiac signal portion ratio analysis, according to invention principles.

FIG. 7 shows an artificial neural network (ANN) 607 employed in signal analyzer 19 in system 10 (FIG. 1) for heart performance characterization and multi-signal channel signal ratio analysis for cardiac malfunction localization and severity characterization. Multi-signal channel cardiac signal ratio analysis provides more precise information about cardiac function status and pathology events. System 10 records and compares calculated signal ratios for signals from different leads of a multi-channel (lead) catheter from different regions of the heart (different tissue, such as atrium, ventricle) and determines ratio variance used by system 10 together with lead location, in identifying malfunction location and severity. Signal analyzer 19 produces a substantial number of ratio analysis results for a particular heart beat cycle and verifies and combines results for a cardiac event monitoring decision using an ANN (Artificial Neural Network) system, for example. Signal analyzer 19 performs multi-signal channel signal portion ratio processing and computations for ANN data input. Specifically, signal analyzer 19 provides, time domain segmented cardiac signal ratios 620 using surface ECG and intra-cardiac signals and frequency domain ratios 623 including dominant frequency ratios and principal frequency ratios of multi-signal channel electrograms as well as other kinds of signal ratios 626 in different domains. ANN unit 607 may alternatively comprise other functions such as a Fuzzy model or expert system model.

ANN unit 607 performs cardiac arrhythmia analysis and detection. The ANN 607 calculation and decision module has self-learning capability processing new input data to increase the accuracy and precision of calculated results. ANN unit 607 is trained for versatile diagnosis and determination of characteristics including arrhythmia type, severity and treatment priority categorization. The ANN based ratio analysis is extended to use additional patient information including, patient history data, vital signs data, hemodynamic data, and data derived by analysis and calculation, for example. Thereby the system determines characteristics of patient pathologies and cardiac malfunctions.

In the system of FIG. 7 ANN unit 607 maps segmented cardiac time domain signal ratios 620, frequency domain signal ratios 623 and other ratios 626 to candidate diagnosis and treatment suggestions. The ANN unit 607 structure comprises 3 layers, an input layer 610, hidden layer 612 and output layer 614. ANN unit $A_{ij}$ weights are applied between input layer 610 and hidden layer 612 components of the ANN computation and $B_{pq}$ weights are applied between hidden layer 612 and calculation index components 614 of the ANN computation. The $A_{ij}$ weights and $B_{pq}$ weights are adaptively adjusted and tuned using a training data set. ANN unit 607 incorporates a self-learning function that processes signal ratios 620, 623 and 626 to increase the accuracy and precision of calculated results. ANN unit 607 analyzes input signal ratios by performing pattern analysis to identify pertinent ratio patterns in a heart chamber, for example, and mapping determined ratio patterns to a candidate diagnosis or treatment decision to localize a tissue impairment within an organ and determine time of occurrence within a heart cycle. ANN unit 607 also identifies arrhythmia type (e.g., AF, MI, VT, VF), severity of arrhythmia treatment and urgency level and is usable for automatic heart condition detection, diagnosis, warning and treatment. Further unit 607 performs statistical analysis to construct a threshold used to detect tissue impairment and diagnose and predict cardiac arrhythmia and pathology.

Following a training phase with a training data set, ANN unit 607 processes signal ratios 620, 623 and 626 to provide a 3D cardiac electrophysiological function mapping to data indicating an Arrhythmia type, Arrhythmia severity, candidate treatment suggestions, localized tissue impairment information identifying the cardiac arrhythmia position, pathology conducting sequence, abnormal tissue area and focus of the disorder and irregularity, for example. System 10 analyzes cardiac electrophysiological signals (including ECG and internal cardiac electrograms) based on a multichannel and multi-segment signal portion ratio calculation and mapping to identify cardiac disorders, differentiate cardiac arrhythmias and quantitative and qualitative analysis and characterization of cardiac pathology and events. The severity threshold of the pathology decision may vary from person to person and is adjusted at the beginning of analysis and in one embodiment may be dynamically adjusted in response to a signal quality or noise measurement, for example. Since the signal analyzer 19 signal portion ratio calculation and analysis require relatively limited computation power, it may be advantageously utilized in general patient monitoring, implantable cardiac devices for real time automatic analysis and detection of cardiac arrhythmias and abnormalities.

Figure 8:
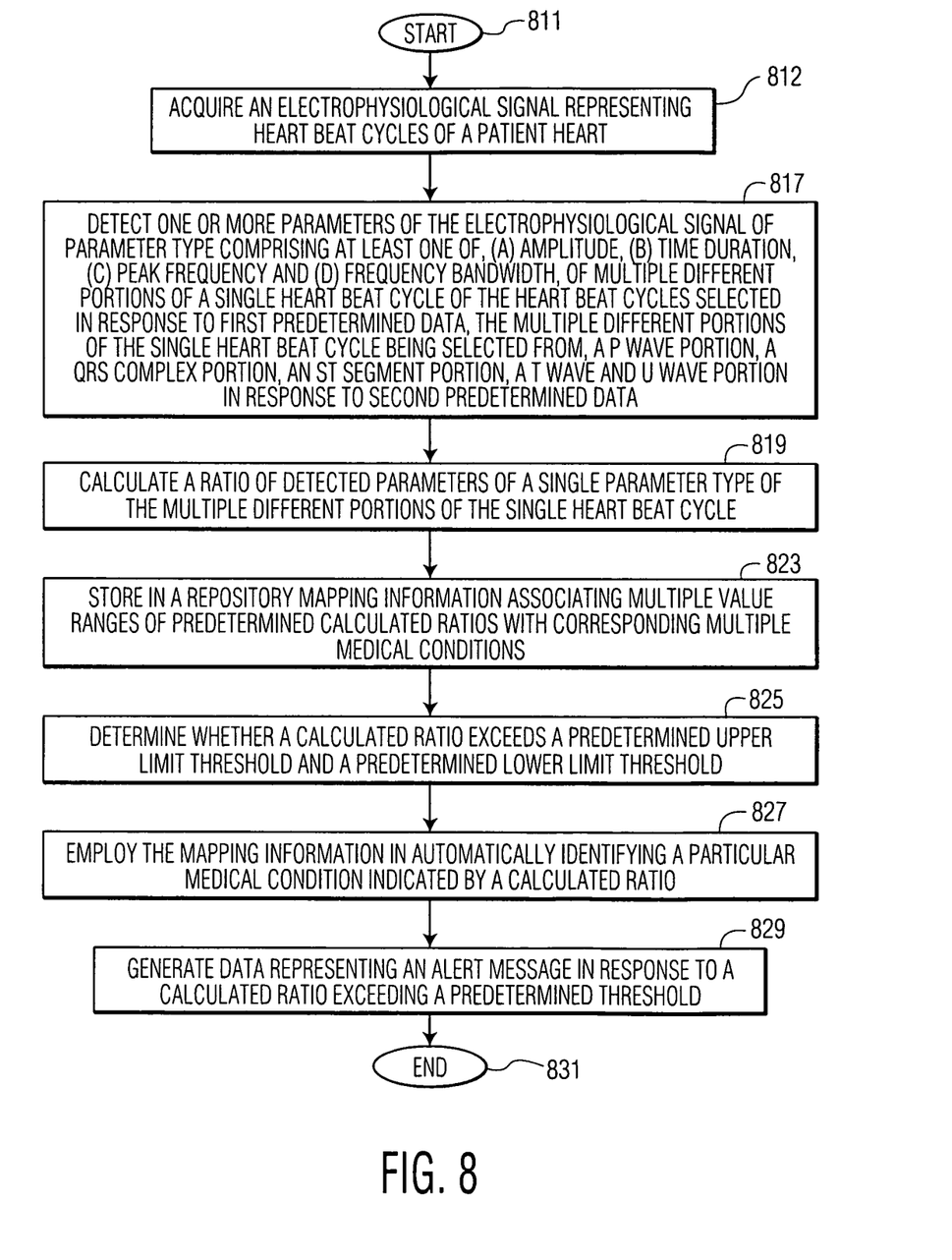
FIG. 8 shows a flowchart of process performed by a system for heart performance characterization and abnormality detection, according to invention principles.

FIG. 8 shows a flowchart of process performed by system 10 (FIG. 1) for heart performance characterization and abnormality detection. In one embodiment, the process of FIG. 8 is performed by a system comprising a patient monitoring device. In step 812 following the start at step 811, acquisition device 15 acquires an electrophysiological signal representing heart beat cycles of a patient heart. In step 817, detector 34 detects one or more parameters of the electrophysiological signal of parameter type comprising at least one of, (a) amplitude, (b) time duration, (c) peak frequency and (d) frequency bandwidth, of multiple different portions of a single heart beat cycle of the heart beat cycles selected in response to first predetermined data. The multiple different portions of the single heart beat cycle are selected from, a P wave portion, a QRS complex portion, an ST segment portion, a T wave and a U wave portion in response to second predetermined data. The first predetermined data and the second predetermined data comprise at least one of, (a) default data and (b) data provided in response to user command.

In step 819, signal analyzer 19 calculates a ratio of detected parameters of a single parameter type (e.g., of amplitude, time duration, peak frequency or frequency bandwidth) of the multiple different portions of the single heart beat cycle. Detector 34 detects maximum or minimum signal amplitude of the different portions of the single heart beat cycle and signal analyzer 19 calculates a ratio of maximum signal amplitude or minimum signal amplitude of the different portions of the single heart beat cycle. Signal analyzer 19 calculates a ratio of time duration of a first combination of the multiple different portions of the single heart beat cycle to a second combination, different to the first combination, of the different portions of the single heart beat cycle. Detector 34 further detects maximum or minimum signal amplitude of a first combination and a second combination of the different portions of the single heart beat cycle and signal analyzer 19 calculates a ratio of maximum signal amplitude or minimum signal amplitude of the first combination and the second combination of the different portions of the single heart beat cycle. Further, detector 34 detects a peak signal frequency of the first combination and the second combination of the different portions of the single heart beat cycle and signal analyzer 19 calculates a ratio of a peak signal frequency of the first combination and the second combination of the different portions of said single heart beat cycle. In addition, detector 34 detects a frequency bandwidth of the first combination and the second combination of the different portions of the single heart beat cycle and signal analyzer 19 calculates a ratio of frequency bandwidth of the first combination and the second combination of the different portions of the single heart beat cycle.

Detector 34 detects a peak signal frequency of the different portions of the single heart beat cycle and signal analyzer 19 calculates a ratio of peak signal frequency of the different portions of the single heart beat cycle. Also detector 34 detects a frequency bandwidth of the different portions of the single heart beat cycle and signal analyzer 19 calculates a ratio of frequency bandwidth of the different portions of the single heart beat cycle. In step 823, signal analyzer 19 stores in repository 17, mapping information associating multiple value ranges of predetermined calculated ratios with corresponding multiple medical conditions including arrhythmia, myocardial infarction and myocardial ischemia. The medical conditions are determined from a population having similar demographic characteristics to the patient, including age, height, weight, gender and pregnancy status. The mapping information also associates the multiple value ranges of predetermined calculated ratios with at least one of, (a) a normal indication and (b) an abnormal indication.

Comparator 31 in step 825 determines whether a calculated ratio exceeds a predetermined upper limit threshold or a predetermined lower limit threshold and signal analyzer 19 in step 827 uses the mapping information in automatically identifying a particular medical condition indicated by a calculated ratio or a ratio value range identified by the determination of step 825. In step 829 output processor 36 generates data representing an alert message in response to a calculated ratio exceeding a predetermined threshold or a predetermined combination of calculated ratios exceeding a predetermined threshold. The alert message initiates treatment by at least one of, (a) initiating drug delivery and (b) initiating electrical stimulus or pacing of a heart. The alert message also indicates severity of a cardiac condition and provides advance warning of myocardial ischemia or acute myocardial infarction in cases including non-symptomatic cases. The process of FIG. 8 terminates at step 831.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system employs cardiac signal portion ratio analysis of cardiac electrophysiological signals and uses predetermined mapping information to associate particular ratio values to a corresponding particular medical condition and determine an accurate time, location and severity of cardiac pathology and events. Further, the processes and applications may, in alternative embodiments, be located on one or more (e.g., distributed) processing devices on the network of FIG. 1. Any of the functions and steps provided in FIGS. 1-8 may be implemented in hardware, software or a combination of both.

What is claimed is:

1. A system for heart performance characterization and abnormality detection, comprising:
    an acquisition device configured for acquiring an electrophysiological signal representing heart beat cycles of a patient heart;
    a detector configured for detecting parameters of said electrophysiological signal of parameter type comprising at least one of, (a) Principal frequency, (b) dominant frequency ratio and (c) frequency bandwidth, of first and second single different portions of a plurality of different portions of a single heart beat cycle of said heart beat cycles selected in response to first predetermined data, said first and second single different portions of said single heart beat cycle individually comprising single different portions selected from, a P wave portion, a QRS complex portion, an ST segment portion and a T wave portion in response to second predetermined data;
    a signal analyzer configured for calculating a ratio of the detected parameters of a single parameter type of the first and second single different portions; and
    an output processor configured for generating data representing an alert message in response to the calculated ratio exceeding a predetermined threshold.

2. A system according to claim 1, wherein
    said detector detects a time duration parameter of said first and second single different portions and
    said signal analyzer calculates both a frequency parameter type ratio and a time duration parameter type ratio using the detected parameters and
    said output processor generates data representing an alert message in response to the calculated ratios.

3. A system according to claim 1, including
    a comparator for determining whether a calculated ratio exceeds a predetermined upper limit threshold or a predetermined lower limit threshold wherein said signal analyzer automatically selects said ratio to calculate and said first and second single different portions of said single heart beat cycle from said P wave portion, said QRS complex portion, said ST segment portion and said T wave portion in response to data indicating a clinical application.

4. A system according to claim 1, including
    a repository of mapping information associating a plurality of value ranges of predetermined calculated ratios with a corresponding plurality of medical conditions,
    said signal analyzer uses said mapping information in automatically identifying a particular medical condition indicated by the calculated ratio and
    said alert message identifies said particular medical condition.

5. A system according to claim 4, wherein
    said mapping information associates said plurality of value ranges of predetermined calculated ratios with at least one of, (a) a normal indication and (b) an abnormal indication.

6. A system according to claim 4, wherein
    said plurality of medical conditions include at least two of, (a) arrhythmia (b) myocardial infarction and (c) myocardial ischemia.

7. A system according to claim 4, wherein
    said mapping information associates a plurality of value ranges of predetermined calculated ratios with a corresponding plurality of medical conditions determined from population having similar demographic characteristics to said patient, said demographic characteristics including at least two of age, height, weight, gender and pregnancy status.

8. A system according to claim 1, wherein
    said signal analyzer automatically selects said ratio of the detected parameters of a single parameter type of the first and second single different portions to calculate, in response to data indicating a clinical application and
    said first predetermined data and said second predetermined data comprise at least one of, (a) default data, (b) data provided in response to user command and (c) data indicating said clinical application.

9. A system for heart performance characterization and abnormality detection, comprising:
    an acquisition device configured for acquiring an electrophysiological signal representing heart beat cycles of a patient heart;
    a detector configured for detecting time duration of first and second single different portions of a plurality of different portions of a single heart beat cycle of said heart beat cycles selected in response to first predetermined data, said first and second single different portions of said single heart beat cycle individually comprising single different portions selected from, a P wave portion, a QRS complex portion, an ST segment portion and a T wave portion in response to second predetermined data;
    a signal analyzer configured for automatically calculating a plurality of different ratios of the time duration of different first and second single different portions of said single heart beat and automatically selecting said ratios to calculate and said first and second single different portions of said single heart beat cycle from said P wave portion, said QRS complex portion, said ST segment portion and said T wave portion in response to data indicating a clinical application; and
    an output processor configured for generating data representing an alert message in response to the calculated ratios exceeding a predetermined threshold.

13

10. A system according to claim 9, wherein
said detector detects a frequency parameter of said first and second single different portions and
said signal analyzer calculates both a frequency parameter type ratio and a time duration parameter type ratio using the detected parameters.

11. A system according to claim 9, wherein
said detector detects a peak signal frequency of said different portions of said single heart beat cycle and
said signal analyzer calculates a ratio of peak signal frequency of said different portions of said single heart beat cycle.

12. A system according to claim 9, wherein
said detector detects a frequency bandwidth of said different portions of said single heart beat cycle and
said signal analyzer calculates a ratio of frequency bandwidth of said different portions of said single heart beat cycle.

13. A system according to claim 9, wherein
said detector detects a U-wave portion of said single heart beat cycle and
said signal analyzer calculates a ratio of the detected parameters of a single parameter type of different portions of said single heart beat cycle.

14. A system according to claim 9, wherein
said signal analyzer calculates a plurality of ratios of time duration of said plurality of different portions of said single heart beat cycle and
said output processor generates data representing an alert message in response to a predetermined combination of the calculated ratios exceeding a predetermined threshold.

15. A system according to claim 9, wherein
said system comprises a patient monitoring device,
said detector detects maximum or minimum signal amplitude of said different portions of said single heart beat cycle and
said signal analyzer calculates a ratio of maximum signal amplitude or minimum signal amplitude of said different portions of said single heart beat cycle.

16. A system according to claim 9, wherein
said alert message indicates severity of a cardiac condition.

17. A system according to claim 9, wherein
said alert message provides advance warning of myocardial ischemia or acute myocardial infarction in cases including non-symptomatic cases.

18. A system according to claim 9, wherein
said alert message initiates treatment by being adapted to at least one of, (a) initiate drug delivery and (b) initiate electrical stimulus or pacing of a heart.

19. A method for heart performance characterization and abnormality detection, comprising the activities of:
acquiring an electrophysiological signal representing heart beat cycles of a patient heart;
detecting time duration of a plurality of different portions of a single heart beat cycle of said heart beat cycles selected in response to first predetermined data, said plurality of portions of said single heart beat cycle being selected from, a P wave portion, a QRS complex portion, an ST segment portion and a T wave portion in response to second predetermined data;
calculating a ratio of time duration of a first combination of said plurality of different portions of said single heart beat cycle to a second combination, different to said first combination, of said different portions of said single heart beat cycle; and
generating data representing an alert message in response to a calculated ratio exceeding a predetermined threshold.

20. A method according to claim 19, wherein
said activity of detecting time duration comprises detecting maximum or minimum signal amplitude of said first combination and said second combination of said different portions of said single heart beat cycle and
said activity of calculating a ratio comprises calculating a ratio of maximum signal amplitude or minimum signal amplitude of said first combination and said second combination of said different portions of said single heart beat cycle.

21. A method according to claim 19, wherein
said activity of detecting time duration comprises detecting a peak signal frequency of said first combination and said second combination of said different portions of said single heart beat cycle and
said activity of calculating a ratio comprises calculating a ratio of a peak signal frequency of said first combination and said second combination of said different portions of said single heart beat cycle.

22. A method according to claim 19, wherein
said activity of detecting time duration comprises detecting a frequency bandwidth of said first combination and said second combination of said different portions of said single heart beat cycle and
said activity of calculating a ratio comprises calculating a ratio of frequency bandwidth of said first combination and said second combination of said different portions of said single heart beat cycle.

23. A method for heart performance characterization and abnormality detection, comprising the activities of:
acquiring an electrophysiological signal representing heart beat cycles of a patient heart;
detecting parameters of said electrophysiological signal of parameter type comprising at least one of, (a) Principal frequency, (b) dominant frequency ratio and (c) frequency bandwidth, of first and second single different portions of a plurality of different portions of a single heart beat cycle of said heart beat cycles selected in response to first predetermined data, said first and second single different portions of said single heart beat cycle individually comprising single different portions selected from, a P wave portion, a QRS complex portion, an ST segment portion and a T wave portion in response to second predetermined data;
calculating a ratio of the detected parameters of a single parameter type of said plurality of the first and second single different portions; and
generating data representing an alert message in response to the calculated ratio exceeding a predetermined threshold.

24. A method according to claim 23, including the activities of
detecting a time duration parameter of said first and second single different portions and
calculating both a frequency parameter type ratio and a time duration parameter type ratio using the detected parameters.

* * * * *